United States Patent [19]

Mookherjee et al.

[11] Patent Number: 5,321,005

[45] Date of Patent: * Jun. 14, 1994

[54] FLAVOR AND FRAGRANCE COMPOSITIONS PRODUCED USING PROCESS FOR QUANTITATIVELY AND QUALITATIVELY SUBSTANTIALLY CONTINUOUSLY ANALYZING THE AROMA EMITTED FROM A LIVING FRUIT

[75] Inventors: Braja D. Mookherjee, Holmdel; Robert W. Trenkle, Brielle; Michael J. Zampino, Roselle Park; Richard A. Wilson, Westfield; Subha M. Patel, Bridgewater, all of N.J.

[73] Assignee: International Flavors & Fragrances Inc., New York, N.Y.

[ * ] Notice: The portion of the term of this patent subsequent to May 11, 2010 has been disclaimed.

[21] Appl. No.: 108,793

[22] Filed: Aug. 19, 1993

Related U.S. Application Data

[63] Continuation-in-part of Ser. No. 988,337, Dec. 9, 1992, Pat. No. 5,269,169.

[51] Int. Cl.$^5$ ............................................. A61K 7/46
[52] U.S. Cl. .................................................... 512/5
[58] Field of Search ................................... 512/2, 5

[56] References Cited

U.S. PATENT DOCUMENTS 2,256,772  9/1941  Freudenberg ........................ 512/5
3,150,050  9/1964  Safrin .................................. 512/5
4,257,945  3/1981  Martel ................................. 512/2

OTHER PUBLICATIONS

Fenaroli, Handbook of Flavor Ingredients, vol. 2, pp. 589-592 (1975).

*Primary Examiner*—James H. Reamer
*Attorney, Agent, or Firm*—Arthur L. Liberman

[57] ABSTRACT

A process for producing flavor and fragrance compositions by means of first quantitatively and qualitatively substantially continuously analyzing the aroma emitted and rates of emission of the components thereof:

(I) from within; and
(II) from the outer surface of a living fruit using simultaneously-operating aroma trapping devices connected to (a) the outer surface of the living fruit and (b) an internal portion of the living fruit, and then providing and admixing at least the major components found in the analysis or analyses. The living fruit may, for example, be a living pineapple or a living nectarine growing on a nectarine tree.

3 Claims, 8 Drawing Sheets

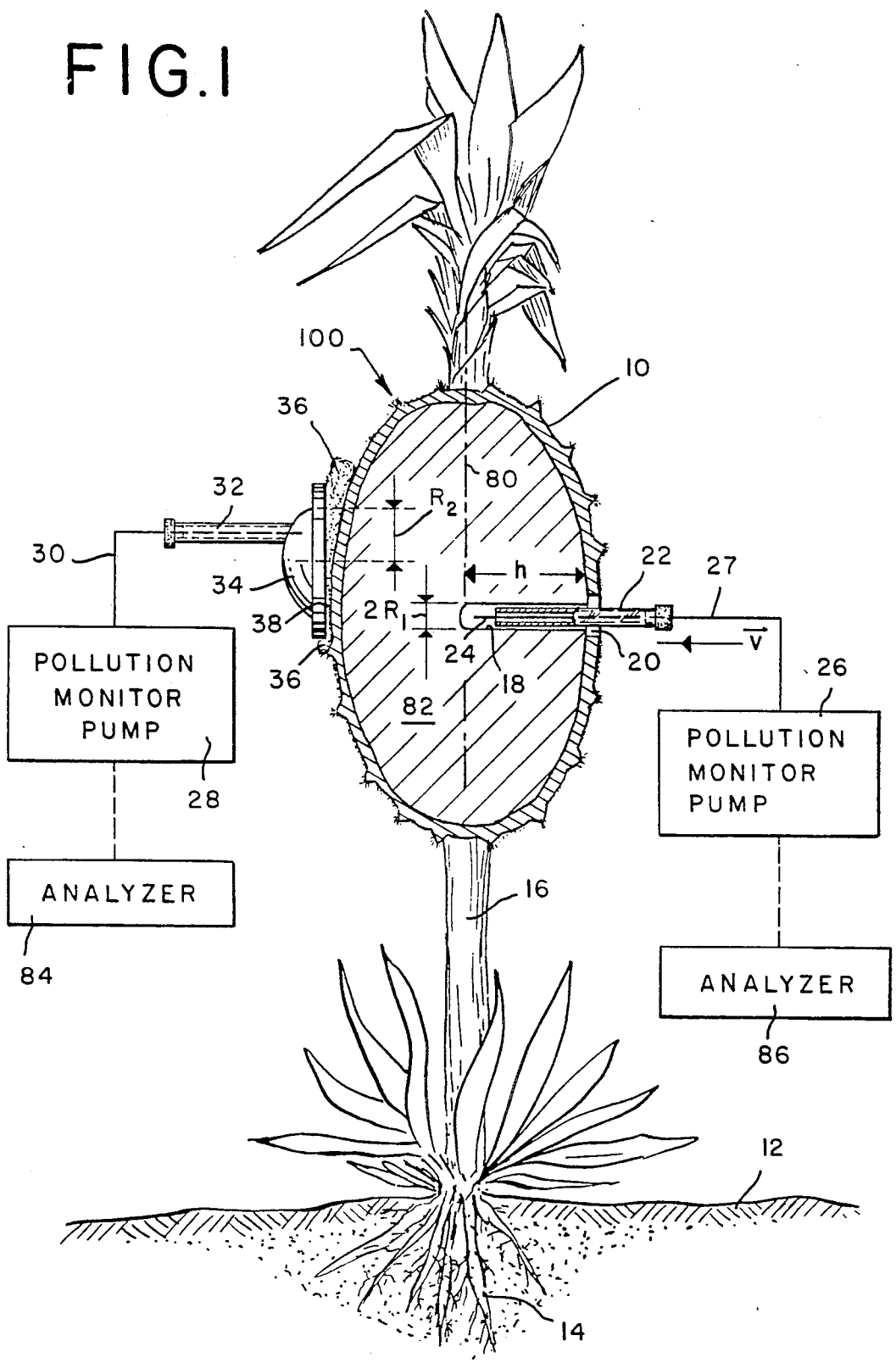

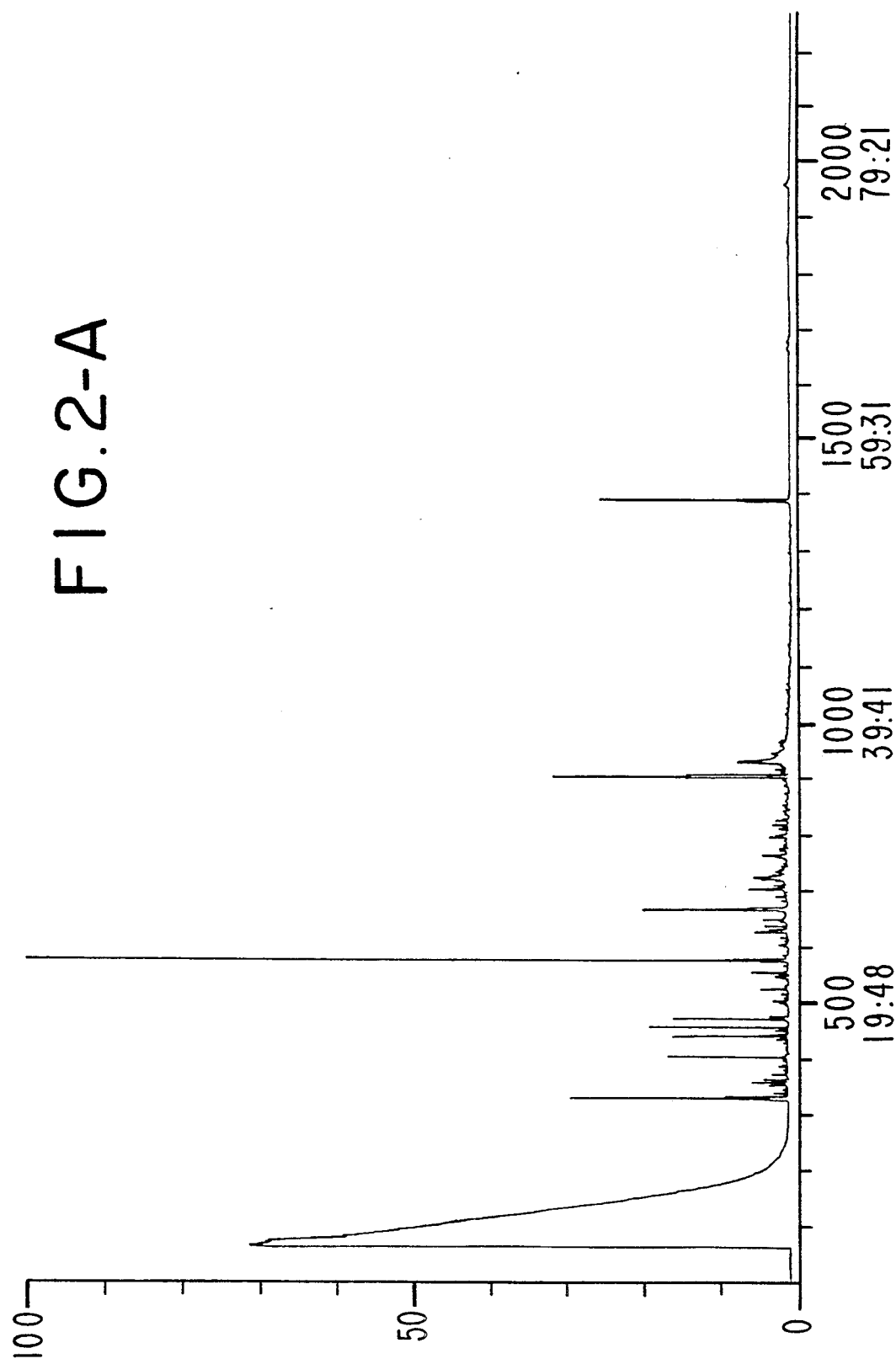

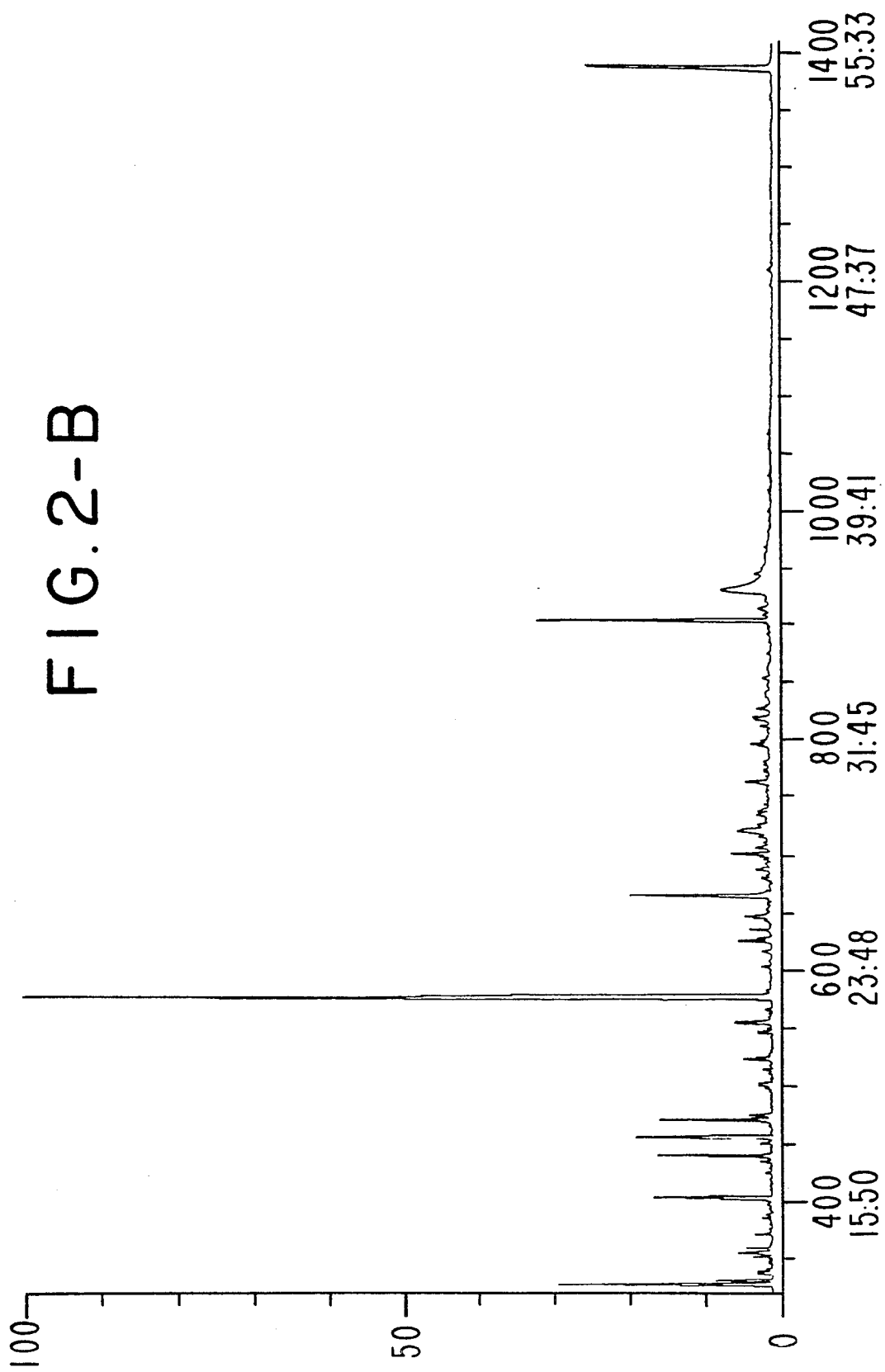

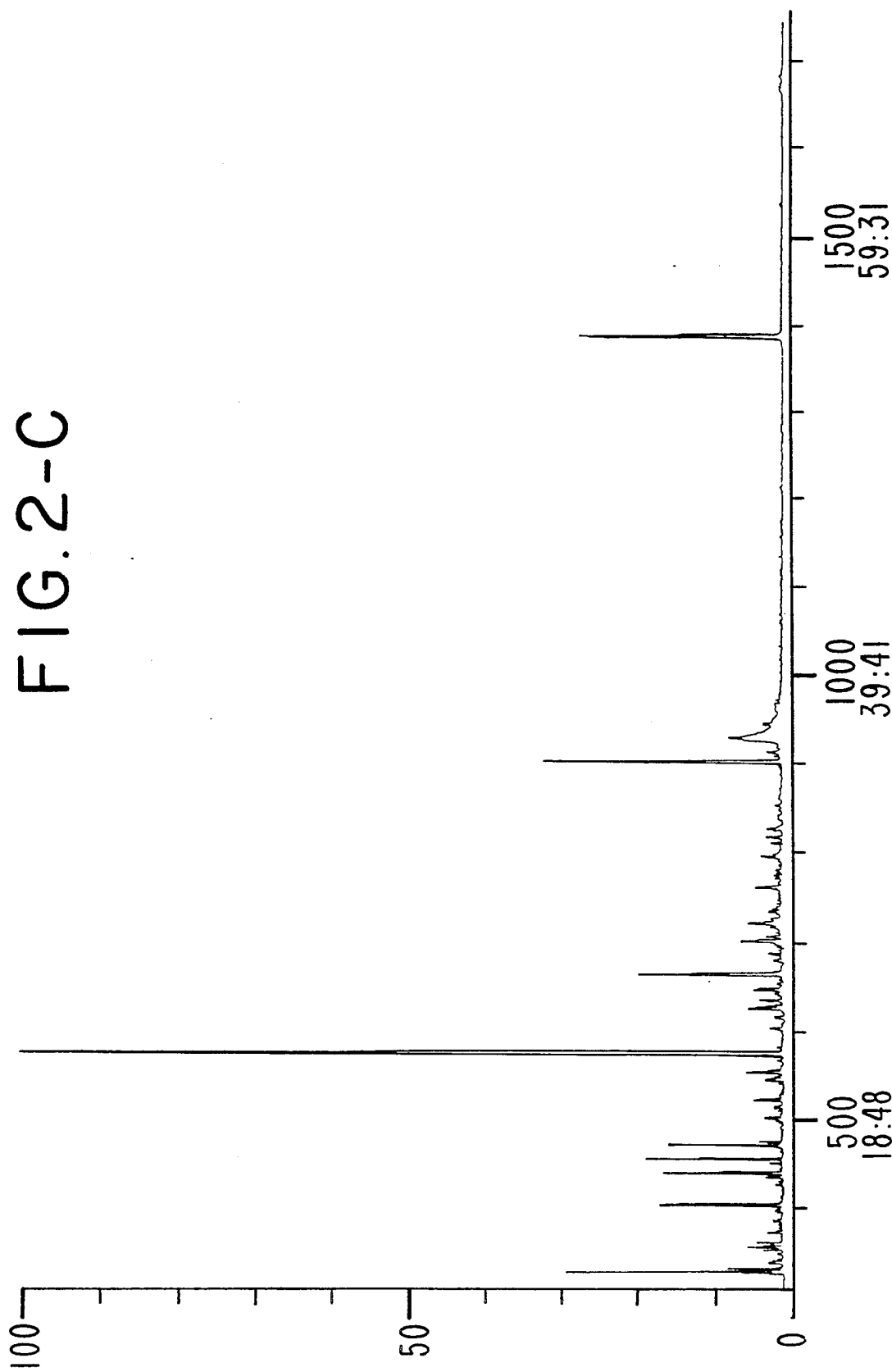

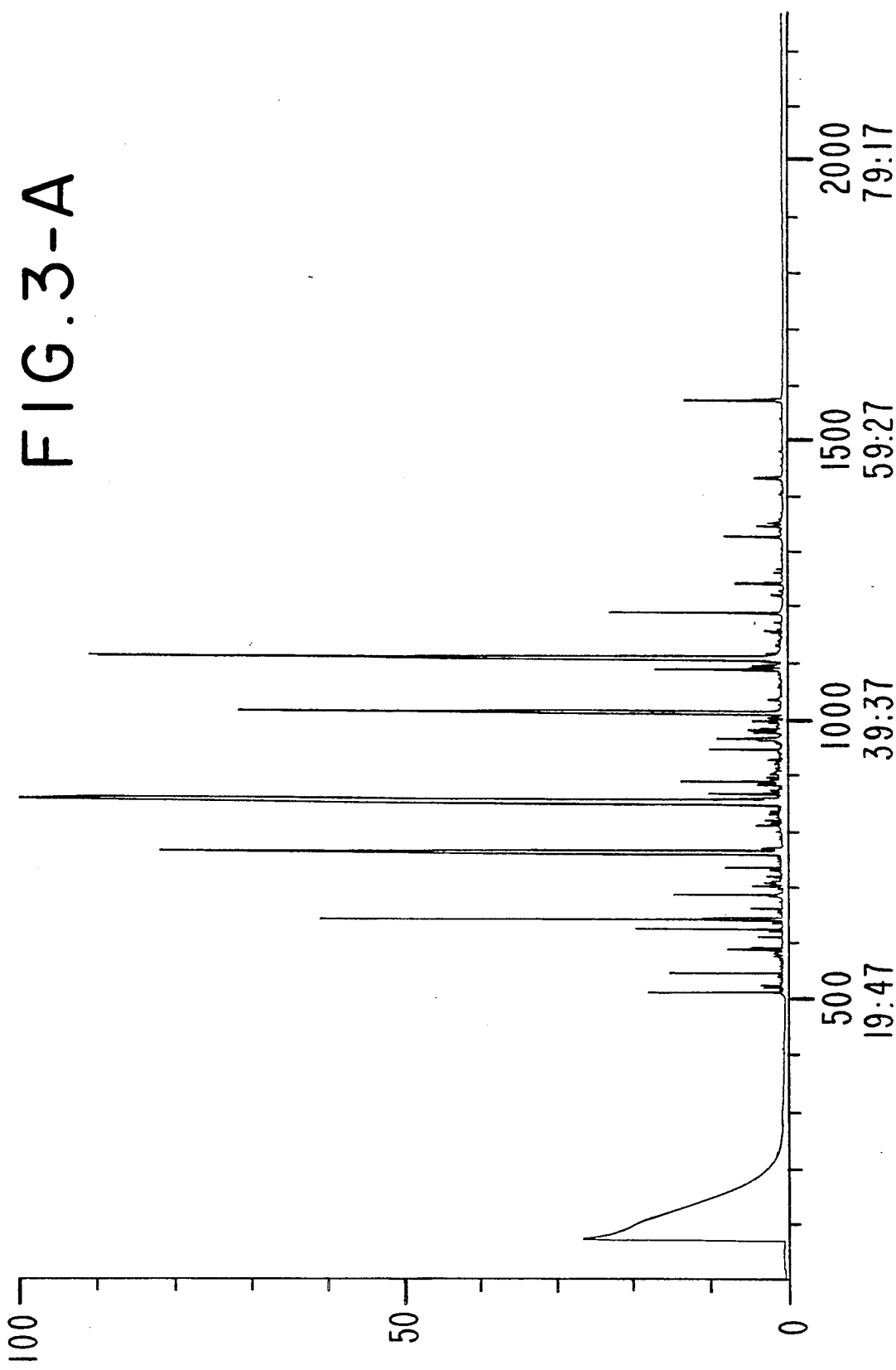
FIG. 3-A

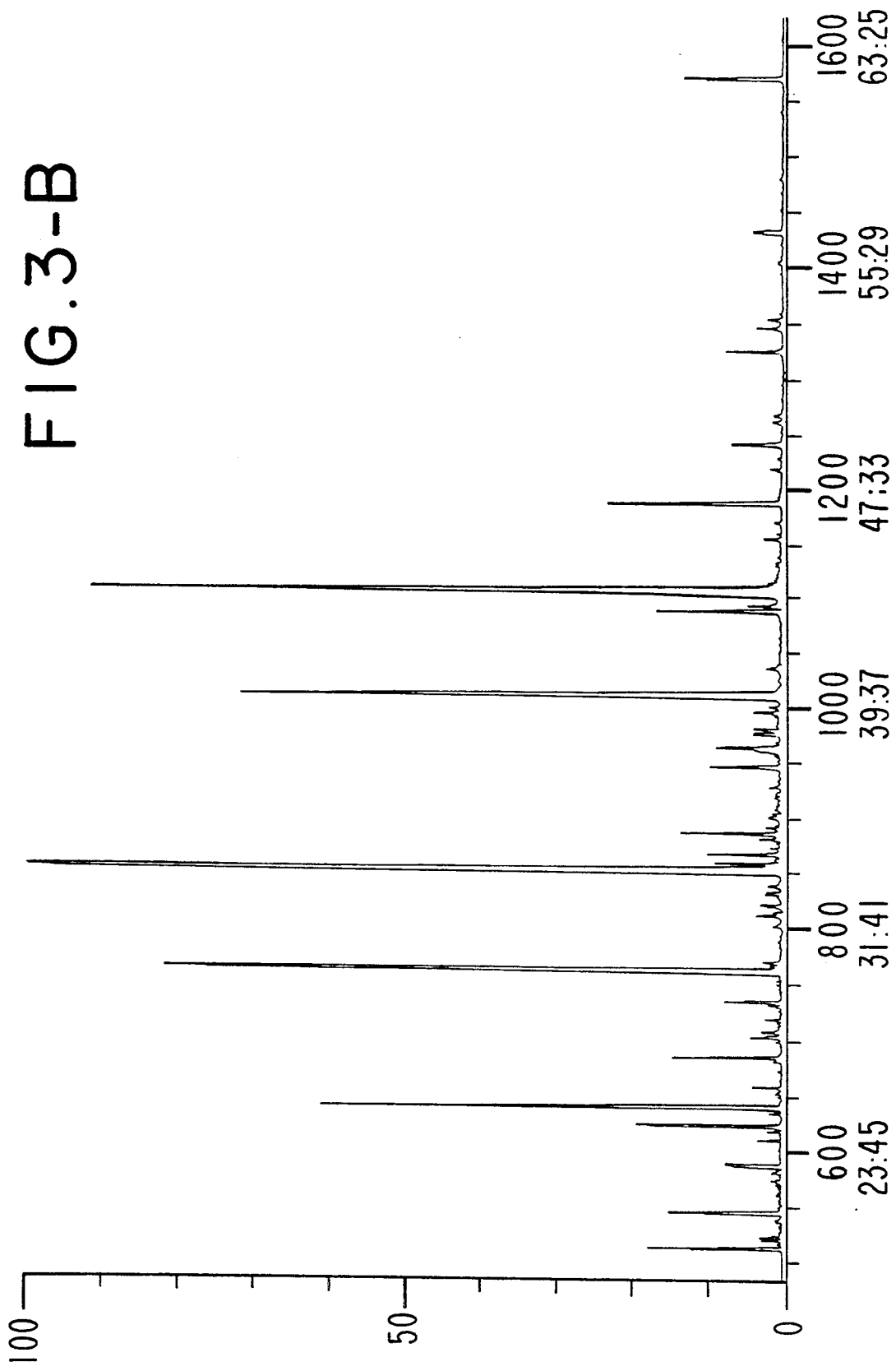

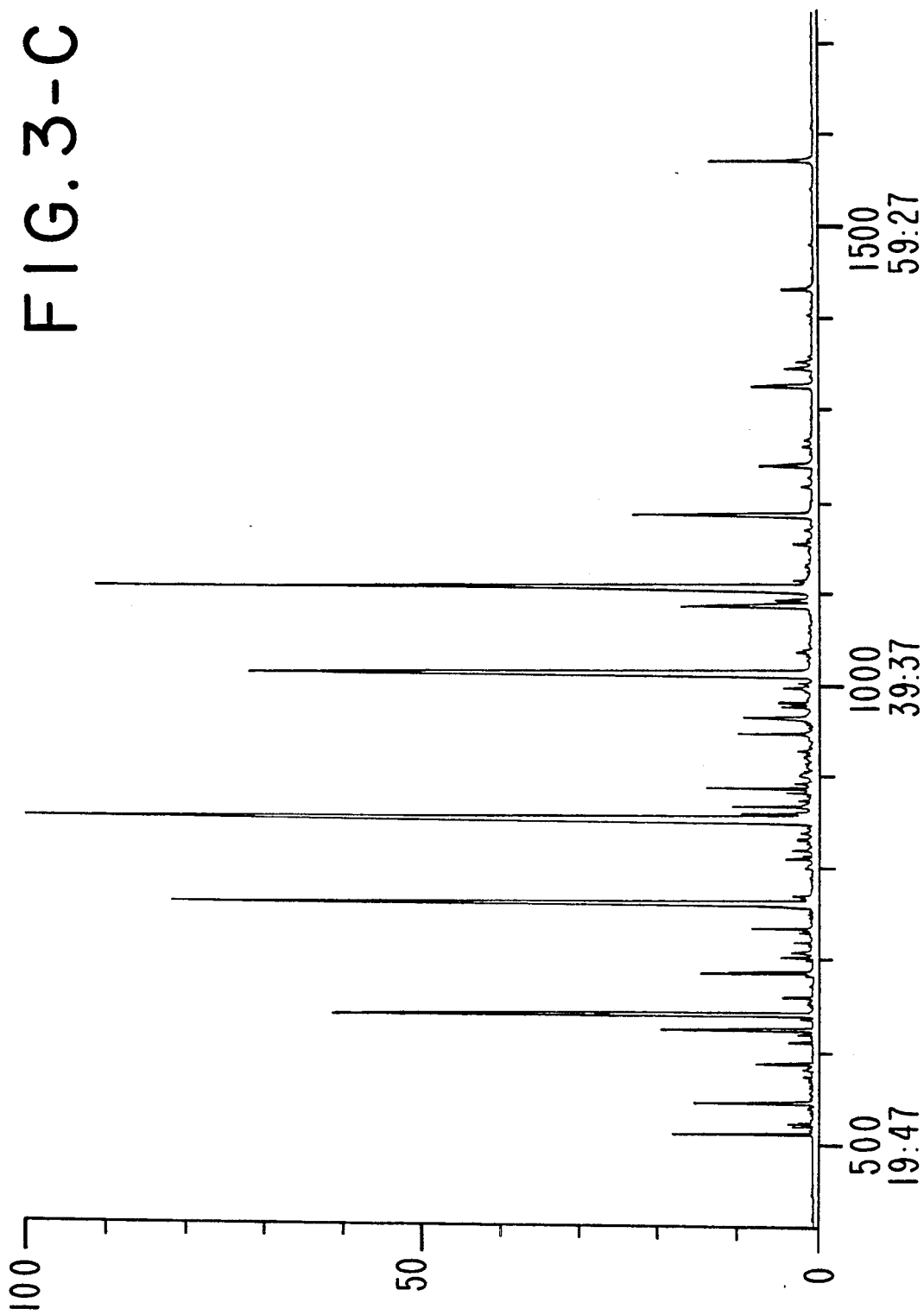
FIG. 3-C

FLAVOR AND FRAGRANCE COMPOSITIONS PRODUCED USING PROCESS FOR QUANTITATIVELY AND QUALITATIVELY SUBSTANTIALLY CONTINUOUSLY ANALYZING THE AROMA EMITTED FROM A LIVING FRUIT

RELATED COPENDING APPLICATIONS

This application is a continuation-in-part of application for U.S. patent, Ser. No. 988,337 filed on Dec. 9, 1992 now U.S. Pat. No. 5,269,169 issued on Dec. 14, 1993.

BACKGROUND OF THE INVENTION

Our invention concerns a process for producing flavor and fragrance compositions by means of quantitatively and qualitatively substantially continuously analyzing the aroma emitted and rates of emission of the components thereof from within and from the outer surface of a living fruit simultaneously and then providing and admixing at least the major components found in the resulting analysis or analyses.

Uses of aromas evolved from living fruits are highly sought after in the perfumery and flavor arts. Great difficulty has been experienced in attempting to capture and reproduce actual aroma ingredients of the living fruit.

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the head space in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Pat. No. 5,136,805 does not teach or infer a technique for producing flavor and/or fragrance compositions by means of quantitatively and qualitatively substantially continuouosly analyzing the aroma emitted and rates of emission of the components thereof from within and the from the outer surface of a living fruit simultaneously and then providing and admixing at least the major components found in the resulting analysis or analyses.

SUMMARY OF THE INVENTION

Our invention is drawn to a process for producing flavors and fragrance compositions by means of quantitatively and qualitatively substantially continuously analyzing the aroma emitted and rates of emission of the components thereof:

(i) from within; and (ii) from the outer surface of a living fruit, simultaneously and then providing and admixing at least the major components found as a result of the carrying out the analysis or analyses.

Examples of such living fruits are living pineapples and living nectarines. Examples of living nectarines are nectarines growing on a tree such as the red jewel nectarine tree (disclosed and claimed in U.S. Plant Pat. No. 8,013 issued on Oct. 27, 1992) and the red diamond nectarine tree (disclosed and claimed in U.S. Plant Pat. No. 3,165).

Our process comprises the steps of:

(a) removing a cylindrical core section from a section of the living fruit to form a core void;

(b) placing a first trapping tube (connected to a vacuum pump) into the core void;

(c) applying an enclosure containing a second trapping tube (connected to a vacuum pump) to a portion of unbroken surface of the same living fruit in a sealably affixable manner;

(d) engaging both vacuum pumps; and (e) analyzing the substances trapped and the trapping tubes on a substantially continuous basis.

Apparatus for carrying out such a process is also intended to be part of our invention.

DETAILED DESCRIPTION OF THE INVENTION

Our invention covers a process for producing flavor and fragrance compositions by means of quantitatively and qualitatively substantially continuously analyzing the aroma emitted and rates of emission of the components thereof:

(i) from within; and (ii) from the outer surface of a living fruit simultaneously consisting essentially of the steps of:

(a) providing a living fruit located on a given central axis having an outer surface, a substantial portion of which is located at a given distance from the central axis and an inner volume surrounding said central axis and encompassed by said outer surface;

(b) removing a depth core section from said inner volume running from said outer surface to a depth of from about halfway up to entirely to the central axis, into said inner volume along a directional vector extending substantially radially from said central axis to said outer surface within said inner volume;

(c)-1: providing first analytical apparatus means comprising a first trapping tube means attached to first negative pressure pump means associated with first chemical analysis means (e.g., GC-mass spectral and infrared analytical equipment);

(c)-2: providing second analytical apparatus means comprising a second trapping tube means attached to second negative pressure pump means associated with second chemical anaylsis means;

(d) providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;

(e) causing said enclosure means to sealably grip said portion of said outer surface of said living fruit at said enclosure rim means;

(f) inserting said first trapping tube means into said core section void along said directional vector;

(g) inserting said second trapping tube means through said insertion orifice causing it to be extended into said enclosure means void;

(h) simultaneously engaging said first negative pressure pump means and said second pressure pump means whereby components of the aroma evolving from said outer surface of said living fruit are entrapped in said second trapping tube means and components of the aroma evolving from within said living fruit are entrapped in said first trapping tube means, simultaneously;

(j) analyzing the contents of said first trapping tube means using said first chemical analysis means and said second trapping tube means using said second chemical analysis means substantially continuously and substantially simultaneously;

(k) providing from at least one independent source at least the major aroma components found in at least one of the two analyses of step (j); and (m) admixing the resulting components to form a perfume composition and/or a flavor composition.

Of course, when the living fruit is one that has a pit such as a peach or a nectarine or a plum, then obviously the depth core can only extend to the outer surface of the pit and preferably the depth core should extend about two-thirds of the way into the fruit without touching the surface of the pit. Thus, for example, in the case of a pineapple the depth core would be about ¼" in diameter and the tube entering the core containing trapping material would be approximately 3/16" in diameter and about 6" in length. Into the tube would be a trap such as a TENAX ® which would be ⅛" in diameter and 4" in length, for example.

Thus, various trapping materials are useful in the practice of our invention in both the trap used in trapping the materials emitted from within the living fruit and entrapping the materials emitted from the outer surface of the living fruit. As stated, supra, TENAX ® is a preferable material. Various forms of TENAX ® are useful, for example, TENAX ®-GC. TENAX ® is a registered trademark of ENKA N.V. of The Kingdom of The Netherlands (CAS Registration No. 24938-68-9). Various forms of TENAX ® and methods of producing such forms of TENAX ® are described in the following U.S. patent the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleneoxide) from its blends with other polymers")

U.S. Pat. No. 3,703,564 issued on Nov. 21, 1972 ("Bis[Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition")

TENAX ®-GC is actually a polyphenyleneoxide defined according to the structure:

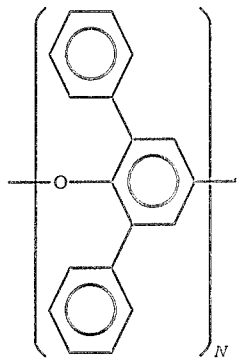

wherein N is an integer of from about 100 up to about 150.

Other trapping materials are as follows: Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1 and 24, 227-6); Activated Alumina marketed by Sigma Chemical Company of St. Louis, Mo. (Catalog Nos. A8753; A8878; A9003; A1772; A1522 and A2272); Silica Gels marketed by Sigma Chemical Company, for example, Catalog Nos. S4004; S6628 and H8506; CHROMOSORB ® (registered trademark of the Johns-Manville Company of Manville, N.J.) such as CHROMOSORB ® such as LC-1; CHROMOSORB ® LC-2; CHROMOSORB ® LC-3, and CHROMOSORB ® LC-7 marketed by the Sigma Chemical Company under Catalog Nos. C 0641; C 0766, C 5517 and C 6269.

The negative pressure pump means of our invention is preferably a vacuum pump of the "Low Flow" variety, for example, "Low Flow" pumps marketed by the Ametek Company of Largo, Fla. 34643 (the Ametek Constant Flow Sampler).

At least one of the living fruit fragrance compositions produced according to the process of our invention and one or more auxiliary perfume ingredients including, for example, alcohols, aldehydes, nitriles, esters, cyclic esters, ketones, ethers, synthetic essential oils and natural essential oils may be admixed so that the combined odors of the individual components produce a pleasant and desired fragrance particularly and preferably in the floral fragrance area.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the overall effect of the perfume composition will be the sum of the effects of each of the ingredients. Thus, one or more of the living fruit fragrance compositions of our invention and one or more auxiliary perfume ingredients can be used to alter the aroma characteristics of a perfume composition, for example, by utilizing or moderating the olfactory reaction contributed by at least one other ingredient in the composition.

The amount of at least one of the living friut fragrance compositions of our invention useful in perfume compositions for augmenting or enhancing of fruity aromas may vary from about 1% by weight of the perfume composition up to 100% by weight of the perfume composition (the entire composition can be composed of the living fruit fragrance components determined by the practice of our invention).

At least one of the living fruit compositions of our invention and, if desired, one or more auxiliary perfume ingredients can be used to impart fruity aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the weight of the perfumed article and will depend upon considerations of cost, nature of the end product, the effect desired on the finished product and the particular fragrance sought.

At least one of the living fruit fragrance compositions of our invention and, if desired, one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE ®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders such as talcs, dusting powders, face powders and the like.

When used as an olfactory component in perfume compositions or perfumed articles, such as anionic, cationic, nonionic, or zwitterionic detergents and fabric softener compositions and fabric softener articles (e.g., for use in clothing dryers) as little as 0.05% of at least one of the living fruit fragrance compositions of our invention and, if desired, one or more auxiliary perfume ingredients will suffice to impart various fruity aroma nuances. Generally, no more than 0.05% of at least one of the living fruit perfume compositions of our invention and, if desired, one or more auxiliary perfume ingredients based on the ultimate end product is required in the perfumed article.

In addition, the perfume composition or fragrance composition of our invention can contain a vehicle or carrier for at least one of the living fruit perfume compositions of our invention and, if desired, one or more auxiliary perfume ingredients. The vehicle can be a liquid such as a non-toxic alcohol, a non-toxic glycol or the like. The carrier can also be an absorbent solid, such as a gum (e.g., gum arabic, xantham gum or guar gum) or components for encapsulating the composition (such as gelatin as by means of coacervation).

When the living fruit compositions of our invention are used as food flavor adjuvants, or are used to augment or enhance the flavor or aroma characteristics of foodstuffs, the nature of the co-ingredients included with the said living fruit compositions in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solids and liquids, and ingestible materials or chewable but non-ingestible materials such as chewing gum. Such materials ususally do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the living fruit compositions, non-reactive with the living fruit compositions of our invention and "ingestibly" acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan, cellulose and cellulose derivatives such as carboxymethyl cellulose and methyl cellulose; natural and synthetic gums, such as gum arabic, gum tragacanth; gelatin, proteinaceous materials, lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetayl, beta,beta-dimethyl acrolein, n-hexanal, 2-hexenal, cis-3-hexenal, 2-heptanal, 4(p-hydroxyphenyl)-2-butanone, alpha-ionone, beta-ionone, methyl-3-butanone, 2-pentanone, 2-pentenal and propanal; alcohols such as 1-butanal, benzyl alcohol, 1-boroneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara yara, natural raspberry oil and vanilla; lactones sulfides, e.g., methyl sulfide and other materials such as maltol, pulegone mercaptan, alpha-phellandrene, ethyl maltol, 2,2,4,4,6,6-hexamethyl-S-trithiane, acetoin and acetals, (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the living fruit compositions can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of living fruit compositions employed in a particular instance can vary over a relatively wide range whereby to its desired organoleptic effects having reference to the nature of the product are achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter the organoleptic characteristics of the parent composition, whether foodstuff per se or flavoring composition.

The use of insufficient quantities of living fruit compositions will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of living fruit compositions ranging from a small but effective amount, e.g., about 0.1 parts per million up to about 50 parts per million by weight based on total composition (more preferably, from about 0.2 ppm up to about 10 ppm) are suitable. Concentrations in excess of the maximum quantity stated are not normally recommended, since they fail to prove commensurate enhancement of organoleptic properties. In those instances, wherein the living fruit compositions are added to the foodstuff as an integral component of a flavoring composition, it is, of course, essential that the total quantity of flavoring composition employed be sufficient to yield an effective living fruit composition concentration in the foodstuff product.

Food flavoring compositions prepared in accordance with the present invention preferably contain the living fruit compositions in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistence, homogeneity of dispersion, etc. Alternatively, flavoring composition in the form of particulate solids can be conveniently prepared by mixing the living fruit compositions with, for example, gum arabic, gum tragacanth, carageenan and the like, and thereafter spray-drying the resultant mixture whereby to obtain the particular solid product. Pre-prepared flavor mixed in powder form, e.g., a fruit-flavored powder mix, are obtained by mixing the dried solid components, e.g., starch, sugar and the like, and living fruit compositions in a dry blender until the requisite degree of uniformity is achieved.

It is presently preferred to combine with the living fruit compositions, the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;

Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-(rimethoxy benzene);
2-(4-hydroxy-4-methylpentyl) norbornadiene;
Natural black currant juice;
Buchu leaf oil;
Alpha-phellandrene;
Cis-3-hexen-1-ol;
Terpinenol-4;
Ethyl maltol;
Methyl benzoate;
Benzaldehyde;
Coriander oil;
alpha-ionone;
Ethyl heptanoate;
Methyl anthranilate;
Ethyl anthranilate;
Cinnamic alcohol;
Amyl valerinate;
Cinnamyl proprionate;
Rhodinyl acetate;
Methyl Beta-hydroxy butyrate;
Ethyl Beta-hydroxy butyrate;
2-Phenyl-3-carboethoxyfuran;
Cyclohexyl disulfide;
Grapefruit oil;
Nootkatone;
Bergamot oil;
Citral;
Amyl alcohol;
5-Phenyl-4-pentenal;
5-Phenyl-2-pentenal;
Allyl caproate;
2-(n-Pentyl) thiazole;
2-(i-Butyl) thiazole;
2-(i-Propyl) thiazole;
2-(n-Propyl) thiazole;
2-Phenyl-4-pentenal;
2-Phenyl-4-pentenaldimethylacetal;
Methional;
4-Methylthiobutanal;
2-Ethyl-3-acetylpyrazine;
Tetramethyl pyrazine;
2-Methyl pyrazine;
Trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thriobutanal-S-oxide;
Thioethanal-S-oxide;
Thiohexanal-S-oxide; and
Propyl propene thiosulfonate.

An additional aspect of our invention provides an organoleptically improved smoking tobacco product and additives therefor, as well as methods of making the same which overcome problems heretofore encountered in which desired sweet, fruity flavor characteristics and aroma characteristics of natural tobacco (prior to smoking and on smoking in the main stream and in the side stream) are created or enhanced or modified or augmented and may be readily controlled and maintained at the desired uniform level regardless of variations in the tobacco components of the blend.

This invention further provides improved tobacco additives and methods whereby various natural aromatic tobacco flavoring characteristics with sweet and fruity notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more living fruit compositions of our invention.

In addition to the living fruit compositions of our invention, other flavoring and aroma additives may be added to the smoking tobacco material or substitute therefor either separately or in mixture with the living fruit compositions as follows:

I. SYNTHETIC MATERIALS

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-ene;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)-furan
4-Hydroxyhexanoic acid, gamma lactone; and
Polyisoprenoid hydrocarbons defined in Example V of U.S. Pat. No. 3,589,372 issued on Jun. 29, 1971.

II. NATURAL OILS

Celery seed oil;
Coffee extract;
Bergamot oil;
Cocoa extract;
Nutmeg oil; and
Origanum oil.

An aroma and flavoring concentrate containing one or more living fruit compositions of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of sweet and/or fruity notes, we have found that satisfactory results are obtained if the proportion by weight of the sum total of living fruit composition(s) to smoking tobacco material is between 50 ppm and 1,500 ppm (0.015%–0.15%). We have further found that satisfactory results are obtained if the proportions by weight of the sum total living fruit composition used to flavoring material is between 1,500 and 15,000 ppm (0.15%–1.5%).

Any convenient method for incorporating the living fruit composition(s) into the tobacco product may be employed. Thus, the living fruit composition(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the living fruit composition(s) taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated by the living fruit composition(s) have in excess of the amounts or concentrations above indicated so that when blended with other tobaccos, the final product will have the percentage within the indicated range.

In accordance with one specific example of our invention an aged, cured and shredded domestic burley tobacco is sprayed with a 20% ethanol solution of a living fruit composition of Example III, infra, in an amount of mixture to provide tobacco composition containing 800 ppm by weight of the mixture of the living fruit composition on a dry basis. Thereafter the alcohol is removed by evaporation and the tobacco is manufactured into cigarettes by the usual techniques. The cigarette when treated as indicated has a desired and pleasing aroma which is detectable in the main stream and the side stream when the cigarette is smoked. This aroma is described as being sweeter, fruity, more aromatic, more tobacco-like having sweet, fruity notes.

While our invention is particularly useful in the manufacture of smoking tobacco such as cigarette tobacco, cigar tobacco and pipe tobacco, other tobacco products formed from sheeted tobacco dust or fines may also be used. Likewise, the living fruit composition(s) of our invention can be incorporated with material such as filter tip materials (e.g., cellulose acetate filters wherein sweet, fruity effects are desired), seam paste, packaging materials and the like which are used along with tobacco to form a product adapted for smoking. Furthermore, the living fruit composition(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent that the living fruit composition(s) of our invention can be utilized to alter, modify or enhance sensory properties, particularly organoleptic properties such as fragrances of a variety of consumable materials including perfume compositions, perfumed articles and colognes and such as aromas and tastes of a variety of consumable materials including smoking tobacco compositions, smoking tobacco articles, foodstuffs, chewing gums, toothpastes, chewing toaccos and medicinal products.

BRIEF DESCRIPTION OF THE DRAWINGS

FIG. 1 is a schematic drawing showing a cut-away side elevation view of a pineapple being quantitatively and qualitatively substantially continuously analyzed for the aroma emitted and rate of emission of the components thereof:

(i) from within; and (ii) from the outer surface of the pineapple simultaneously.

FIG. 2A is the GC mass spectrum of the composition of the aroma produced by carrying out Example I, infra, of the interior of a living pineapple.

FIG. 2B is an enlarged portion of the GC mass spectrum of FIG. 2A.

FIG. 2C is another enlarged portion of the GC mass spectrum of FIG. 2A.

FIG. 3A is the GC mass spectrum of the aroma emitted from the external surface of a pineapple in Example I, infra, using the apparatus shown in FIG. 1.

FIG. 3B is an enlarged portion of the GC mass spectrum of FIG. 3A.

FIG. 3C is another enlarged portion of the GC mass spectrum of FIG. 3A.

Figure 4:
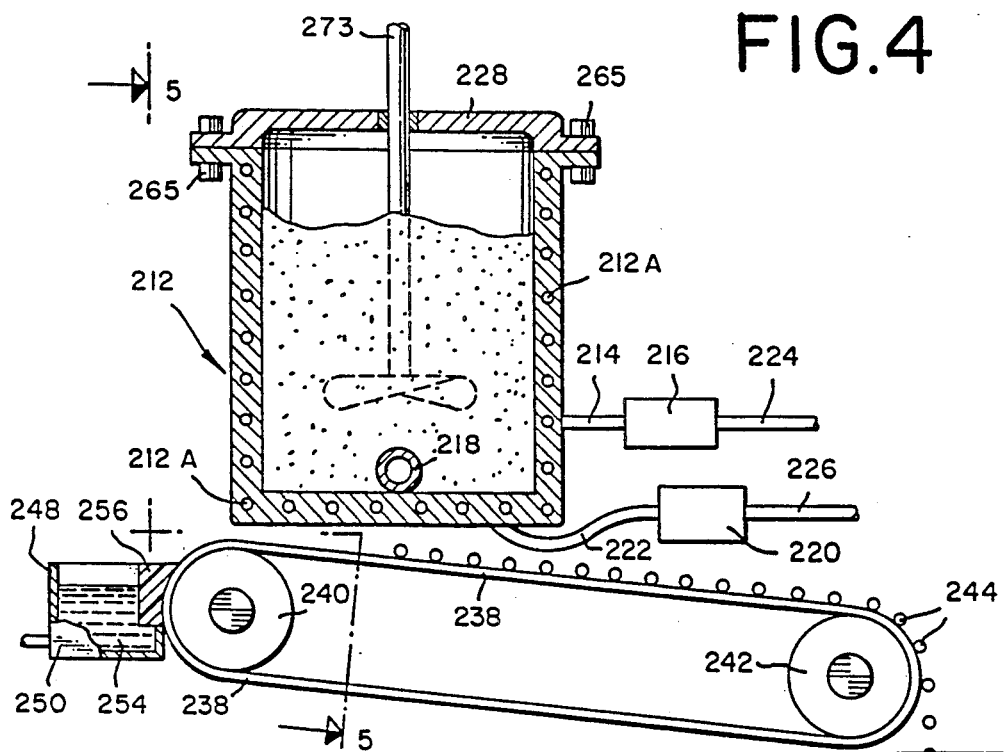

FIG. 4 represents a cut-away side elevation view of apparatus used in forming perfumed polymers containing at least one of the living fruit compositions of our invention.

Figure 5:
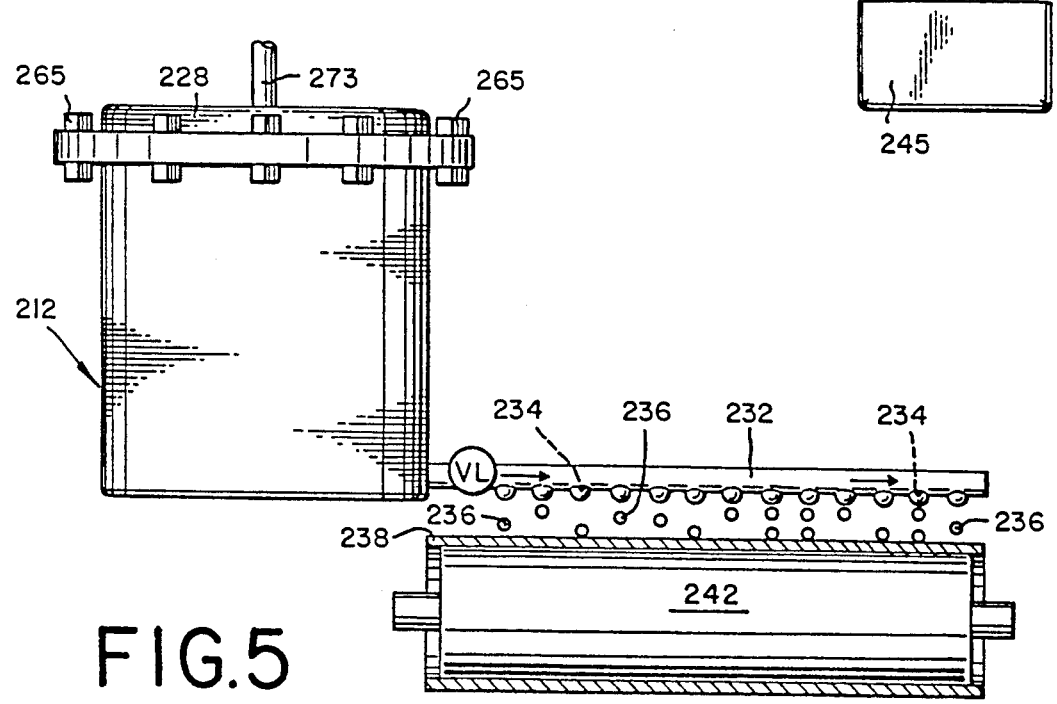

FIG. 5 is a front view of the apparatus of FIG. 4 looking in the direction of the arrows.

DETAILED DESCRIPTION OF THE DRAWINGS

Referring to FIG. 1, a living pineapple having access 80 and roots 14 living in ground 12 having an inner volume 82 and a surface 10 is shown having the aroma and rate of emission of the components thereof:

(i) from within the pineapple; and (ii) from the outer surface of the pineapple being analyzed simultaneously.

A substantial portion of the outer surface 10 is located at a given distance "h" (e.g., 6") from the central axis 80 and an inner volume 82 surrounds the central axis 80 and is encompassed by the outer surface 10; and a depth core section 18 is removed from the inner volume 82 along a directional vector "V" extending substantially radially from the central axis 80 to the outer surface 10 within the inner volume 82. The depth core section 18 has effective diameter, $D_1$ (e.g., about $\frac{1}{4}$") equal to $2 \times$ (the effective radius $R_1$ (about $\frac{1}{8}$")) and a core section volume ranging from about $[\pi R_1^2 h]$ down to about $\left[\dfrac{\pi R_1^2 h}{2}\right]$ thereby forming a core section void within the living fruit. First analytical apparatus means in FIG. 1 comprises a first trapping tube means (22, 24) which is a glass outer tube 22 and a trapping tube 24 inserted through opening 20 into depth core 18. Attached to the trapping tube 24 (which may, for example, contain 10× ® GC) is tube 27 connected to a negative pressure pump means 26.

Reference numeral 86 represents analytical apparatus capable of providing GC-mass spectra of trapped substances which may be taken further together with spectral apparatus capable of providing infrared spectra of the trapped substances and apparatus capable of providing NMR (nuclear magnetic resonance) spectra of the trapped substances.

Second analytical apparatus means (for analyzing the aroma emitted from the surface of the pineapple of FIG. 1) comprises second trapping tube means 32 inserted into enclosure 34 which is sealably affixed at 36 (a sealing material is indicated by reference numeral 36) to a portion of the surface of the pineapple 38. The trapping tube means is connected to tube 30 which is connected to negative pressure pump 28 associated with analyzer 84 (e.g., GC-mass spectral analyzer; nuclear magnetic resonance analyzer; and infrared analyzer). The apparatus is maintained in place in conjunction with the living fruit, e.g., the living pineapple of FIG. 1 which is held up by living pineapple stem 16. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$[\tfrac{2}{3}\pi R_2^3]$.

Thus, when the first negative pressure pump means 26 and the second negative pressure pump means 28 are simultaneously engaged, components of the aroma evolving from the outer surface of the living fruit (e.g., the pineapple shown by reference numeral 100) are entrapped in the second trapping tube means 32 and the first trapping tube means 22 simultaneously, enabling the contents of the first trapping tube means and the second trapping tube means to be continuously analyzed substantially simultaneously using said first and second chemical analysis means 86 and 84, respectively.

Referring to FIGS. 4 and 5, there is provided a process for forming scented polymer pellets (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 4 and 5, in particular, the apparatus used in producing such elements comprises a device for forming the polymer containing perfume, e.g., polyethylene or polyethylene-polyvinyl acetate or mixtures of same or polypropylene, or the like, which comprises a vat or container 212 into which the polymer taken alone or in admixture with other copolymers and a perfuming substance containing at least one of the living fruit fragrances of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds.

Heating means (coils 212A) are operated to maintain the upper portion of the container 212 within a temperature range of, for example, 250°–260° C. in the case of low density polyethylene. The bottom portion of the container 212 is also heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing at least one of the living fruit fragrances of our invention is quickly added to the melt. Generally, about 10–45 percent by weight of the resulting mixture of the perfumery substance is added to the polymer.

After the perfume material containing at least one of the living fruit fragrances of our invention is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "VL" is opened permitting the mass to flow outwardly through conduit 232 (also indicated by reference numeral 218 in FIG. 4) having a multiplicity of orifices 234 adjacent to the lower side thereof. The outer end of the conduit 232 is closed so that the liquid polymer intimately admixed with at least one of the living fruit fragrances of our invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the living fruit fragrances of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

The following examples are illustrative of processes for using the apparatus useful in carrying out our invention, processes for carrying out production of flavor and fragrance formulations of our invention and processes for using the living fruit fragrances and flavors of our invention. These examples are illustrative and the invention is to be considered to be restricted thereto only as indicated in the appended claims.

All parts and percentages given herein are by weight unless otherwise specified.

EXAMPLE I

Head Space Sampling and the Analysis of the Interior and Exterior of a Living Pineapple Fruit

Objective

To analyze the head space of the exterior and interior of a living pineapple fruit to determine, through GC/MS analysis, the difference between the interior and exterior volatile head space constituents.

Procedure

A mature plant containing a ripe orange color pineapple is the subject of the investigation.

To the outside of the fruit was attached one half of a 25 ml clam shaped head space flask with inlet tube and SWAGELOK ® fittings. The unevenness of the pineapple's exterior against the glass head space apparatus was filled in with KIMWIPE ® tissue to make a good seal. A TENAX ® GC head space trap was then inserted into the head space flask, and the exterior head space was sampled for approximately 6-8 hours at a flow of 30 ml/minute.

The interior of the pineapple was bored half way (3.5") with a metal ¼" diameter cork borer. A glass ¼" pyrex tube, 10" in length was inserted into the fruit in a direction towards the central axis of the fruit, halfway between the top and bottom of the fruit. The tube extends 3.5" internally in the fruit and 6.5" externally from the fruit.

A standard TENAX ® trap (approximately 4.5" in length) was then inserted into this ¼" diameter tube. The interior head space of the fruit was then sampled at the same time and same conditions as the exterior head space sampling.

The entrapped interior and exterior pineapple fruit head space was then analyzed by GC/MS as shown in FIGS. 2A, 2B, 2C, 3A, 3B and 3C the analysis is as follows:

TABLE I

| COMPOUND IDENTIFIED | EXTERIOR % | INTERIOR % |
|---|---|---|
| Acetaldehyde | 0.97 | 1.0 |
| Dichloromethane | 0.01 | |
| 2-Butene | 0.03 | |
| Ethanol | 0.01 | |

TABLE I-continued

| COMPOUND IDENTIFIED | EXTERIOR % | INTERIOR % |
|---|---|---|
| Acetone | 0.3 | 0.85 |
| Furan | | 0.01 |
| Methyl Acetate | | 0.01 |
| Isoprene | 0.01 | |
| Acetic Acid | 0.1 | 1.24 |
| Ethyl Acetate | 1.17 | |
| Methyl Propionate | 0.02 | |
| 2-Butenal | 0.01 | |
| Butanol | 0.01 | |
| 2-Methyl Furan | 0.01 | 0.78 |
| 2-Pentanone | 0.01 | |
| Diacetyl | | 0.48 |
| Methyl Isobutyrate | 0.01 | |
| Ethyl Acrylate | 0.01 | |
| 1-Hydroxy 2-Propanone | | 0.36 |
| Ethyl Propionate | 0.17 | 0.01 |
| Methyl Butyrate | 0.73 | 2077 |
| A Methyl Furan | 0.01 | |
| Ethyl Isobutyrate | 0.14 | 0.15 |
| Methyl Crotonate | 0.04 | 0.01 |
| Isoamyl Alcohol | 0.01 | |
| Isobutyl Acetate | 0.06 | |
| Toluene | 0.06 | 0.38 |
| Methyl 2-Methyl Butyrate | 1.79 | 2.82 |
| 2-Hexanone | 0.01 | |
| Hexanal | 0.08 | 0.21 |
| 2-Furan Carboxaldehyde | 0.01 | |
| Ethyl Butyrate | 4.8 | 3.12 |
| Methyl Valerate | 0.23 | 0.01 |
| Furfural | 0.01 | 3.87 |
| Methyl 3-Hydroxy Butyrate | 0.01 | |
| Ethyl 2-Methyl Butyrate | 0.44 | 0.87 |
| Furfuryl Alcohol | | 0.01 |
| Ethyl Isovalerate | 0.01 | |
| Hexanol | 0.36 | |
| Methyl Tiglate | 0.01 | |
| Xylene | 0.33 | 1.11 |
| Ethyl Valerate | | 0.01 |
| 3-Heptanone | 0.01 | |
| 2-Heptanone | 0.22 | |
| Isoamyl Acetate | 0.01 | |
| Ethyl Valerate | 0.69 | 0.01 |
| Citraconic Anhydride | | 1.22 |
| Heptanal | 0.01 | 0.71 |
| Methyl Trans-3-Hexenoate | 0.01 | |
| Amyl Acetate | 0.01 | |
| Methyl Hexanoate | 13.14 | 24.56 |
| Benzaldehyde | | 0.07 |
| 5-Methyl Furfural | | 0.3 |
| 3-Methyl 2-Butenyl Acetate | 0.01 | |
| Methyl Trans-3-Hexenoate | 0.19 | |
| Cumene | 0.01 | |
| Propyl Benzene | 0.06 | |
| Methyl Trans 2-Hexenoate | 0.07 | |
| C-3 Benzene Derivative | 0.64 | |
| 2-Octanone | 0.07 | |
| Phenol | 0.08 | 1.25 |
| Ethyl Caproate | 25.56 | 4.74 |
| Ethyl 3-Hexenoate | 0.7 | |
| Cis-3-Hexenyl Acetate | | 0.01 |
| Myrcene | | 0.01 |
| Methyl Sorbate | 0.01 | |
| Methyl 3-Methyl Thiopropionate | 0.88 | 0.45 |
| Decane | 0.12 | 0.45 |
| Methyl Heptanoate | 0.16 | 0.01 |
| Gamma Hexalactone | 0.17 | |
| p-Cymene | 0.01 | 0.01 |
| 2-Ethyl Hexanol | 0.17 | 0.75 |
| Limonene | 0.13 | 0.55 |
| Ethyl 2-Hexenoate | 0.13 | |
| Methyl 3-Hydroxy Hexenoate | 0.01 | |
| Decalin | 0.01 | |
| Octanol | 0.01 | |
| Ethyl Sorbate | 0.01 | |
| Ethyl 3-Methyl Thiopropanoate | 1.05 | |
| Alpha Para Dimethyl Styrene | 0.01 | |
| Ethyl Heptanoate | 0.7 | |
| Methyl Cis-4-Octenoate | 0.37 | |
| Phenyl Ethyl Alcohol | 0.01 | |
| Nonanal | | 1.01 |

TABLE I-continued

| COMPOUND IDENTIFIED | EXTERIOR % | INTERIOR % |
|---|---|---|
| Linalool | | 0.01 |
| Ethyl 2-Ethyl Hexanoate | | 0.25 |
| Undecane | | 0.62 |
| Ethyl 3-Hydroxy Hexanoate | 0.01 | |
| Methyl Octanoate | 9.39 | 0.64 |
| Silicone | 1.83 | 8.77 |
| Ethyl Cis-4-Octenoate | 0.5 | |
| Ethyl Octanoate | 13.4 | 0.01 |
| Methyl 3,5-Acetoxy Hexanoate | 5.36 | 0.61 |
| 5-Hydroxy Methyl Furfural | | 7.86 |
| Decanal | .07 | |
| Citronellal | | 0.01 |
| Ethyl HydroxyOctanoate | 2.31 | |
| Ethyl Nonanoate | 0.01 | |
| Methyl Decanoate | 0.16 | |
| Ethyl Decanoate | 0.41 | |
| 5-Acetyloxy Methyl Octanoate | 0.23 | |
| Alpha Murolene | 1.34 | 1.43 |
| Alpha Copaene | | 0.01 |
| Alpha Caryophellene | | 0.01 |
| Total Percentage Identified: | 93.55 | 76.41 |

EXAMPLE II

As a result of the foregoing analysis as set forth in Table I, supra, the following formulation was prepared using the major components of the "exterior" headspace:

| Ingredients | Parts by Weight |
|---|---|
| Methyl Hexanoate | 13.14 |
| Ethyl Caproate | 25.56 |
| Ethyl 3-Methyl Thiopropanoate | 1.05 |
| Methyl Octanoate | 9.39 |
| Ethyl Octanoate | 13.4 |
| Methyl 3,5-Acetoxy Hexanoate | 5.36 |
| Ethyl Hydroxy Octanoate | 2.31 |
| Ethyl Murolene | 1.34 |
| Ethyl Acetate | 1.17 |
| Methyl 2-Methyl Butyrate | 1.79 |
| Ethyl Butyrate | 4.8. |

The resulting fragrance has an intense and substantive natural pineapple aroma with natural peach and green topnotes and natural apricot undertones. Accordingly, the resulting fragrance can be described as "fruity with natural pineapple and apricot undertones and peach and green topnotes".

EXAMPLE III

As a result of the analysis as set forth in Table I of Example I, supra, the following formulation was prepared using the major components of the "interior" headspace:

| Ingredients | Parts by Weight |
|---|---|
| Methyl Hexanoate | 24.56 |
| Phenol | 1.25 |
| Ethyl Caproate | 4.74 |
| Nonanal | 1.01 |
| 5-Hydroxy Methyl Furfural | 7.86 |
| Alpha Murolene | 1.43 |
| Acetic Acid | 1.24 |
| Methyl Butyrate | 2.77 |
| Methyl 2-Methyl Butyrate | 2.82 |
| Ethyl Butyrate | 3.12 |
| Furfural | 3.87 |
| Citraconic Anhydride | 1.22. |

The resulting fragrance has an intense and substantive natural pineapple aroma with natural peach and green topnotes and natural apricot undertones. Accordingly, the fragrance can be described as "fruity with natural pineapple and apricot undertones and peach and green topnotes".

EXAMPLE IV

As a result of the foregoing analysis as set forth in Table I of Example I, supra, the following formulation was prepared using the major components of the "exterior" combined with the "interior" headspace:

| Ingredients | Parts by Weight |
|---|---|
| Methyl Hexanoate | 37.70 |
| Phenol | 1.25 |
| Ethyl Caproate | 30.30 |
| Ethyl 3-Methyl Thiopropanoate | 1.05 |
| Nonanal | 1.01 |
| Ethyl Octanoate | 9.39 |
| Methyl Octanoate | 13.4 |
| Methyl 3,5-Acetoxy Hexanoate | 5.36 |
| 5-Hydroxy Methyl Furfural | 7.86 |
| Ethyl Hydroxy Octanoate | 2.31 |
| Alpha Murolene | 2.77 |
| Acetic Acid | 1.24 |
| Ethyl Acetate | 1.17 |
| Methyl Butyrate | 2.77 |
| Methyl 2-Methyl Butyrate | 4.54 |
| Ethyl Butyrate | 7.92 |
| Furfural | 3.87 |
| Citraconic Anhydride | 1.22. |

The resulting fragrance has an intense and substantive natural pineapple aroma with natural peach and green topnotes and natural apricot undertones. Accordingly, the resulting fragrance can be described as "fruity with natural pineapple and apricot undertones and peach and green topnotes".

EXAMPLE V

Preparation of a Soap Composition

100 Grams of soap chips are admixed with 1 gram of one of the perfume substances of Table II below until a substantially homogeneous composition is obtained. The perfumed soap manifests an excellent aroma as set forth in Table II below:

TABLE II

| Perfume Ingredients | Aroma |
|---|---|
| Perfume composition of Example II. | Fruity with natural pineapple and apricot undertones and peach ad green topnotes. |
| Perfume composition of Example III. | Fruity with natural pineapple and apricot undertones and peach and green topnotes. |
| Perfume composition of Example IV. | Fruity with natural pineapple and apricot undertones and peach and green topnotes. |

EXAMPLE VI

Preparation of a Cologne and Handkerchief Perfume

One of the perfume substances set forth in Table II of Example V is incorporated into a cologne at concentrations of 1.5%, 2.0%, 2.5%, 3.0%, 3.5% and 4.0% in 80%, 85%, 90% and 95% aqueous ethanol and into handkerchief perfumes at concentrations of 15%, 20%, 25% and 30% (in 85%, 90% and 95% aqueous ethanol). Distinct and definite fragrances as set forth in Table II of Example V are imparted to the cologne and to the handkerchief perfume at each of the levels indicated.

EXAMPLE VII

Preparation of a Cosmetic Powder Composition

A cosmetic powder is prepared by mixing in a ball mill, 100 grams of talcum powder with 0.15 grams of one of the substances of Table II of Example V. The resulting powders have excellent aromas as set forth in Table II of Example V.

EXAMPLE VIII

Utilizing the procedure of Example I of Column 15 of U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo paper");
2. Adogen 448 (m.p. about 140° F.) as the substrate coating; and
3. an outer coating having the following formulation (m.p. about 150° F.):

57 percent—$C_{20-22}$HAPS
   27 percent—isopropyl alcohol
   20 percent—antistatic agent
   1 percent—of one of the perfume substances of Table II of Example V.

Fabric-softening compositions prepared as set forth above having an aroma characteristic as set forth in Table II of Example V essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. Aromas are imparted as set forth in Table II of Example V in a pleasant manner to the headspace in the dryer on operation thereof using the said dryer added fabric softening non-woven fabric.

EXAMPLE IX

Preparation of a Soap Composition

100 Grams of soap chips are prepared according to Example V of U.S. Pat. No. 4,058,490 issued on Nov. 15, 1977 the specification for which is incorporated herein by reference, as follows:

"The sodium salt of an equal mixture of $C_{10}$-$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table II of Example V until a substantially homogeneous composition is obtained. The perfumed soap composition manifests an aroma as set for in Table II of Example V.

EXAMPLE X

Granular Detergent Composition

A granular detergent composition is prepared according to United Kingdom Patent No. 1,501,498 the specification for which is incorporated by reference herein having the following formula. It is prepared by spray-drying the following mixture:

| Ingredient | Parts by Weight |
| --- | --- |
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio $SiO_2/Na_2O = 2.0$ | 6.0 |
| Sodium tripolyphosphate | 24.0 |
| $Na_{12}(AlO_2SiO_2)27H_2O$ | 18.0 |
| Moisture | 10.0 |
| Sodium sulfate | 25.0 |
| Perfume substance of Table II of Example V | 4.0 |

Laundry solutions containing the above detergent compositions are used to launder fabrics. Each of the laundry compositions both prior to and on laundering give rise to a pleasant aroma as set forth in Table II of Example V.

EXAMPLE XI

Perfumed Liquid Detergent

Concentrated liquid detergents are prepared with aromas as set forth in Table II of Example V containing 0.10%, 0.15% and 0.20% of each of the substances of Table II of Example V in the liquid detergent. The liquid detergent is a builder free liquid detergent consisting of (a) 50% of a nonionic surfactant having a HBL of 8.0 and a critical micelle concentration of 0.007 weight percent at 25° C.; (b) an anionic surfactant which is a triethanolamine prepared according to United Kingdom Patent No. 1,491,603 the specification for which is incorporated by reference herein.

The detergents all possess aromas as set forth in Table II of Example V, supra.

EXAMPLE XII

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column 9, U.S. Pat. No. 4,000,080 issued on Dec. 28, 1976, the specification for which is incorporated by reference herein) is intimately admixed with 0.15 grams of one of the perfume materials of Table II of Example V, supra, until a substantially homogeneous composition is obtained. The composition has an aroma as set forth in Table II of Example V, supra.

EXAMPLE XIII

Each of the fragranced material of Table II of Example V, supra, are added to a 50:50 weight:weight mixture of low density polyethylene:polyepsilon caprolactone PCL-700 forming pellets with scents as set forth in Table II of Example V, supra.

75 Pounds of a mixture of PCL-700 polyepsilon caprolactone (manufactured by the Union Carbide Corporation of New York, N.Y. having a melting point of about 180°-190° F.): low density polyethylene are heated to about 250° C., in a container of the kind illustrated in FIGS. 4 and 5. 25 Pounds of each of the fragrance materials as set forth in Table II of Example V is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidified almost instantaneously upon impact with the moving cooled conveyor 238. Polymer beads or pellets 244 having pronounced scents as described in Table II of Example V, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example V, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example V, supra.

EXAMPLE XIV

Each of the LIVING FRUIT TM perfume compositions of Table II of Example V are individually admixed with CLARYCET TM (trademark of International Flavors & Fragrances Inc. for the ester having the structure:

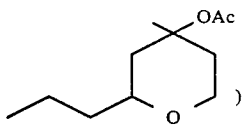

in the ratio of 10 parts by weight of ester to one part by weight of LIVING FRUIT TM perfume composition. At the rates of:
 100 ppm;
 150 ppm; and
 200 ppm
the resulting composition is added to EXXON ® middle distillate fuel heating oil in accordance with the procedure of European Published Application 532,556 published on Mar. 24, 1990 (corresponding to PCT Application 91/18961-A).

On use, in each case, the unpleasant "burnt fuel oil" nuances are completely masked and "faint pleasant aromas" described in Table II of Example V are imparted to the environments surrounding the burning heating oil.

EXAMPLE XV

Raspberry Flavor Formulation

The following basic raspberry flavor formulation is produced:

| Ingredient | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl Butyrate | 6.0 |
| Ethyl Acetate | 16.0 |
| Dimethyl Sulfide | 1.0 |
| Isobutyl Acetate | 13.0 |
| Acetic Acid | 10.0 |
| Acetaldehyde | 10.0 |
| Propylene Glycol | 930.0 |

The LIVING FRUIT TM (Exterior-Interior) formulation produced according to Example IV, supra, is added to half of the above formulation at the rate of 0.2%. The formulation with the living fruit composition produced according to Example IV is compared with the formulation without the living fruit composition produced according to Example IV at the rate of 0.01% (100 ppm) in water and evaluated by a bench panel.

The flavor containing the living fruit composition produced according to Example IV is found to have a substantially more pleasant and better raspberry aroma. It is the unanimous opinion of the bench panel that the living fruit composition produced according to Example IV rounds the flavor out and contributes to a very natural fresh aroma and taste as found in full ripe raspberries. Accordingly, the flavor with the additon of the living fruit composition of Example IV produced according to Example IV is considered as substantially better than the flavor without the living fruit composition produced according to Example IV.

EXAMPLE XVI

Basic Black Currant Formulation

The living fruit composition (exterior) produced according to Example II, supra, has been added to basic black currant flavor formulation at the rate of 1.5%. A second black currant flavor formulation is produced without the living fruit composition. Both flavors have been compared in water at the rate of 200 ppm and evaluated by a bench panel. The flavor containing the living fruit composition of Example II has the characteristic aroma and taste of ripe black currants or fresh black currant juice. This typical note was not present in the basic black currant formulation set forth below. Therefore all members of the panel preferred the flavor containing the living fruit composition. Detailed below is the Basic Black Currant Formulation to which is added in one of the examples the living fruit composition at a rate of 1.5%:

| Ingredient | Parts by Weight |
| --- | --- |
| Cis-3-hexen-1-ol | 5.0 |
| Alpha-phellandrene | 1.5 |
| Terpineol-4 10% (in ethyl alcohol) | 3.0 |
| Para-hydroxy benzyl acetone | 5.0 |
| Vanillin | 2.0 |
| Ethyl maltol | 6.0 |
| Methyl benzoate | 2.0 |
| Benzaldehyde | 2.0 |

| Ingredient | Parts by Weight |
| --- | --- |
| Benzylpropionate | 4.0 |
| Isobutylacetate | 5.0 |
| Coriander oil | 0.5 |
| Ethylbutyrate | 8.0 |
| Dimethylsulfide | 3.0 |
| Fusel oil | 8.0 |
| Acetic acid | 10.0 |
| Alpha-ionone 10% (in ethyl alcohol) | 0.5 |
| Ethyl heptanoate | 0.5 |
| Propylene glycol | 934.0 |
| | 1000.0 |

EXAMPLE XVII (A) 120 Grams of the flavor composition of Example III is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 rpm.

(B) The following mixture is prepared:

| Ingredient | Parts by Weight |
| --- | --- |
| Liquid flavor composition of Example III | 25 |
| Propylene glycol | 1 |
| Cab-O-Sil M-5 (Brand of Silica produced by the Cabot Corporation of 125 High Street, Boston, Massachusetts 02110; Physical properties: surface area: 200 m$^2$/gm Nominal Particle size: 0.012 microns Density: 2.3 lbs./cu. ft.) | 3 |
| Ethyl cellulose | 8 |

The Cab-O-Sil and ethyl cellulose is dispersed in the liquid flavor composition of Example III with vigorous stirring, thereby resulting in a viscous liquid. 65 Parts by weight of the powder flavor composition of Part A is then blended into said viscous liquid, with stirring, at 25° C. for a period of 30 minutes resulting in a dry, free flowing, sustained release flavor powder.

EXAMPLE XVIII

Chewing Gum

200 Parts by weight of chicle are mixed with 4 parts by weight of the flavor prepared in accordance with Example XVII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickenss. The strips are cut into lengths of 3 inches each. On chewing, the chewing gum has a pleasant, long-lasting pineapple flavor.

EXAMPLE XIX

Chewable Vitamin Tablets

The flavor material produced according to Example XVII is added to a chewable vitamin tablet formulation at a rate of 5 gm/Kg which chewable vitamin formulation is prepared as follows:

In a Hobart Mixer, the following materials are blended to homogeneity:

| | Gms/1000 Tablets |
| --- | --- |
| Vitamin C (ascorbic acid) as ascorbic acid-sodium ascorbate mixture 1:1 | 70.0 |
| Vitamin B$_2$ (thiamine mononitrate) as Rocoat thiamine mononitrate 33⅓% (Hoffman La Roche) | 4.0 |
| Vitamin B$_2$ (riboflavin) as Rocoat riboflavin 33⅓% | 5.0 |
| Vitamin B$_6$ (pyridoxine hydrochloride) as Rocoat pyridoxine hydrochoride 33⅓% | 4.0 |
| Niacinamide as Rocoat niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XVII | 2.5 |
| Sweetener - sodium saccharin | 1.0 |
| Magnesium stearate lubricant | 10.0 |
| Mannitol q.s. to make | 500.0 |

Preliminary tables are prepared by slugging with flatfaced punches and grinding the slugs to 14 mesh. 13.5 g Dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong pineapple flavor for a period of 12 minutes.

EXAMPLE XX 0.5% Living fruit flavor of Example IV is added to a commercial quality of grapefruit oil. The oils with and without this chemical are compared in water at the rate of 10 ppm. The aroma and taste characteristics of the modified oil is considered as much more characteristic of grapefruit peel than of the oil without this chemical Therefore, a bench panel unanimously prefers the oil containing the living fruit flavor.

EXAMPLE XXI

The following mixture is prepared:

| Ingredient | Parts by Weight |
| --- | --- |
| Methyl anthranilate | 11.0 |
| Ethyl acetate | 9.0 |
| Ethyl anthranilate | 2.5 |
| Ethyl butyrate | 2.0 |
| Ethyl methyl phenyl glycidate | 1.5 |
| Cinnamic acid | 0.3 |
| Cognac oil | 0.1 |
| Ethyl alcohol | 73.16 |

The above mixture is judged to be an acceptable grape flavor when evaluated in a sweetened and acidified aqueous tasting solution. 1.5 Parts of living fruit is added to the above flavor and a significan improvement in aroma and taste is noted. When this is evaluated in the aforementioned tasting solution, it is judged to have an improved grape character and grape fidelity. It contains more fresh concord grape character, true fruitiness with a nuance of wine. In addition, it is judged to be a more rounded and natural flavor, superior to the product made without the addition of living fruit compositions in both aroma and taste.

Similar results obtained when using 2.5 parts of living fruit compositions prepared according to Example III.

EXAMPLE XXII

Tobacco Formulation

A tobacco mixture is produced by admixing the following ingredients:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 0.1% to all of the cigarettes produced using the above tobacco formulation. Half of the cigarettes are then treated with 500 to 1,500 ppm of the living fruit composition produced according to Example II.

The control cigarettes not containing the living fruit composition and the experimental cigarettes which contain the living fruit composition are evaluated by paired comparision and the results are as follows:

The experimental cigarettes are found, on smoking to have a sweeter, fruity, more natural tobacco-like aroma prior to smoking and on smoking in the main stream and the side stream. The experimental cigarettes containing the product produced according to Example II are basically more burley tobacco-like.

All cigarettes are evaluated for smoke flavor with a 20 mm cellulose acetate filter.

What is claimed is:

1. A process for producing one or more flavor and/or fragrance compositions by means of quantitatively and qualitatively substantially continuously analyzing the aroma emitted and rate of emission of the components thereof:
   (i) from within; and
   (ii) from the outer surface of
   a living fruit, simultaneously, consisting essentially of the steps of:
   (a) providing a living fruit located on a given central axis having an outer surface, a substantial portion of which is located at a given distance, "h" from said central axis and an inner volume surrounding said central axis and encompassed by said outer surface;
   (b) removing a depth core section from said inner volume running from said outer surface to a depth of from about "½h" up to "h" into said inner volume along a directional vector "V" extending substantially radially from said central axis to said outer surface within said inner volume, said depth core section having an effective diameter $D_1$ equal to $2\times$(effective radius, $R_1$) and a core section volume ranging from about $$[\pi R_1^2 h] \text{ down to about } \left[\frac{\pi R_1^2 h}{2}\right]$$

thereby forming a core section void within said living fruit; then
   (c)-1: providing first analytical apparatus means comprising first trapping tube means attached to first negative pressure pump means associated with first chemical analysis means;
   (c)-2: providing second analytical apparatus means comprising a second trapping tube means attached to second negative pressure pump means associated with second chemical anaylsis means:
   (d) providing a hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;
   (e) causing said enclosure means to sealably grip said portion of said outer surface of said living fruit at said enclosure rim means;
   (f) inserting said first trapping tube means into said core section void along said directional vector "V";
   (g) inserting said second trapping tube means through said insertion orifice, causing it to be extended into said enclosure means void;
   (h) simultaneously engaging said first negative pressure pump means and said second negative pressure pump means whereby components of the aroma evolving from said outer surface of said living fruit are entrapped in said second trapping tube means and components of the aroma evolving from within said living fruit are entrapped in said first trapping tube means, simultaneously; and
   (j) analyzing the contents of said first trapping tube means using said first chemical analysis means and said second trapping tube means using said second chemical analysis means substantially continuously and substantially simultaneously;
   (k) providing from at least one independent source at least the major aroma components found in at least one of the two analyses of step (j); and
   (m) admixing the resulting components provided by step (k) to form a perfume composition and/or a flavor composition.

2. The process of claim 1 wherein the living fruit is a living pineapple.

3. The process of claim 1 wherein the living fruit is a living nectarine.

* * * * *